US011033217B2

(12) United States Patent
Wakeham et al.

(10) Patent No.: US 11,033,217 B2
(45) Date of Patent: Jun. 15, 2021

(54) CRANK MEASUREMENT SYSTEM WITH IMPROVED STRAIN GAUGE INSTALLATION

(71) Applicant: 4IIII INNOVATIONS INC., Cochrane (CA)

(72) Inventors: Keith Wakeham, Calgary (CA); Kipling William Fyfe, Cochrane (CA); Billy Cheuk Wai Chan, Calgary (CA); Hamid Ebrahimi Kahaki, Calgary (CA); David McNab, Calgary (CA); Brandon Riches, Cochrane (CA)

(73) Assignee: 4IIII INNOVATIONS INC., Cochrane (CA)

( * ) Notice: Subject to any disclaimer, the term of this patent is extended or adjusted under 35 U.S.C. 154(b) by 105 days.

(21) Appl. No.: 16/087,589

(22) PCT Filed: Mar. 21, 2017

(86) PCT No.: PCT/US2017/023454
§ 371 (c)(1),
(2) Date: Sep. 21, 2018

(87) PCT Pub. No.: WO2017/165448
PCT Pub. Date: Sep. 28, 2017

(65) Prior Publication Data
US 2019/0099119 A1 Apr. 4, 2019

Related U.S. Application Data

(60) Provisional application No. 62/311,367, filed on Mar. 21, 2016.

(51) Int. Cl.
*G01L 1/22* (2006.01)
*A61B 5/22* (2006.01)
(Continued)

(52) U.S. Cl.
CPC .............. *A61B 5/221* (2013.01); *A61B 5/224* (2013.01); *A61B 5/6895* (2013.01); *B62J 6/06* (2013.01);
(Continued)

(58) Field of Classification Search
None
See application file for complete search history.

(56) References Cited

U.S. PATENT DOCUMENTS 5,909,781 A    6/1999 Yonekawa et al.
8,316,709 B2   11/2012 Grab
(Continued)

FOREIGN PATENT DOCUMENTS

JP    5483299 B2    5/2014
WO    2016/030768 A2    3/2016

OTHER PUBLICATIONS

Japanese Patent Application No. 2017-530446, English translation of Office Action dated Sep. 18, 2018, 2 pages.
(Continued)

*Primary Examiner* — Harshad R Patel
*Assistant Examiner* — Nigel H Plumb
(74) *Attorney, Agent, or Firm* — Lathrop GPM LLP

(57) ABSTRACT

A crank measurement system includes four bend-sensing strain gauges located on one surface of a crank and oriented parallel to a neutral axis of the crank to sense bend strain induced in the crank. Two of the bend-sensing strain gauges are located above the neutral axis, and the other two bend-sensing strain gauges are located below the neutral axis. The system also includes two shear-sensing strain gauges located on the one surface and oriented to sense shear strain induced in the crank. The shear-sensing strain gauges are located on opposite sides of the neutral axis. The system may also include up to four axial-sensing strain gauges located on the
(Continued)

one surface and oriented to sense axial strain induced in the crank. An electronics module receives strain data from the strain gauges, and determines from the strain data one or more of force, torque, and power applied to the crank.

10 Claims, 13 Drawing Sheets

(51) Int. Cl.
    *B62M 3/08*     (2006.01)
    *B62M 6/45*     (2010.01)
    *G01L 3/24*     (2006.01)
    *A61B 5/00*     (2006.01)
    *B62J 6/12*     (2006.01)
    *G01L 5/22*     (2006.01)
    *B62J 6/06*     (2006.01)
    *B62M 3/00*     (2006.01)
    *B62J 45/40*     (2020.01)

(52) U.S. Cl.
    CPC ............... *B62J 6/12* (2013.01); *B62M 3/00* (2013.01); *B62M 3/08* (2013.01); *B62M 6/45* (2013.01); *G01L 1/22* (2013.01); *G01L 3/24* (2013.01); *G01L 5/225* (2013.01); *A61B 2503/10* (2013.01); *A61B 2560/0214* (2013.01); *A61B 2562/0261* (2013.01); *B62J 45/40* (2020.02)

(56) References Cited

U.S. PATENT DOCUMENTS

| | | |
|---|---|---|
| 8,825,279 B2 | 9/2014 | Kitamura et al. |
| 2005/0285461 A1 | 12/2005 | Kitamura et al. |
| 2009/0222050 A1 | 9/2009 | Wolter et al. |
| 2011/0109206 A1 | 5/2011 | Li |
| 2012/0330572 A1 | 12/2012 | Longman |
| 2017/0370785 A1 | 12/2017 | Jenn |

OTHER PUBLICATIONS

U.S. Appl. No. 16/114,063, Office Action dated Jun. 24, 2019, 6 pages.

International Search Report and Written Opinion of PCT/US2017/023454 dated Jul. 18, 2017, 14 pp.

CRANK MEASUREMENT SYSTEM WITH IMPROVED STRAIN GAUGE INSTALLATION

RELATED APPLICATIONS

This application is a 35 U.S.C. § 371 filing of International Application No. PCT/US2017/023454, filed Mar. 21, 2017, which claims priority to U.S. patent application Ser. No. 62/311,367, titled "System and Method for Bicycle Power Measurement and Energy Supply", filed Mar. 21, 2016, and incorporated herein by reference. This application is also related to PCT Application Number PCT/IB2015/002099, filed Aug. 26, 2015, entitled "Adhesively coupled Power-Meter for Measurement of Force, Torque, and Power and Associated Methods," which is incorporated as Appendix A of the aforementioned application.

BACKGROUND

Fitness training can be accomplished under several different ideologies such as perceived exertion, heart rate, or power output. These ideologies fall under categories of subjective and objective measures of an athlete's effort. Perceived exertion and heart rate are examples of subjective measure that may vary due to fatigue, temperature, hydration, duration of effort, etc. A power-meter, on the other hand, is an objective device that measures both the torque and angular velocity (in a rotating system) or force and velocity (in a translating system) to determine a rate of energy input to a system. This energy rate is generally measured in Watts or horsepower.

Power-meter use has become very popular for training and racing since it objectively displays the power output by an athlete. This objective measure is more desirable than the subjective measures provided by heart rate monitors for example. The user's heart rate changes during a given exertion and this change typically lags strong efforts resulting in inaccurate indications of effort being exerted by the athlete. Thus, subjectively determined measurements have limitations, whereas power-meter measurements are more accurate and provide near instantaneous feedback without bias.

To measure power input to a bicycle for example, there are several locations where the forces, torques, and/or angular velocities may be measured, including shoe cleats, pedals, crank arms, the spider connecting the cranks to the chain ring, chain, wheel hub, and frame. Power measurement at each of these locations presents challenges, requiring specialized instrumentation by skilled technicians on specially engineered components that are specifically designed for attaching the instrumentation.

FIG. 1 depicts a prior art bicycle pedal-crank assembly 100 that includes a crank 102, having a longitudinal axis X, a vertical axis Y, and a lateral axis Z. This assembly 100 is used for measuring torque being produced by the pedal force in the crank's rotation plane (the X-Y plane). The pedal-crank assembly 100 includes a crank 102, having a top surface 104, a bottom surface 106, an inner surface 108, and an outer surface 110. Crank 102 is attached to a bottom bracket (not shown), that rotates about lateral axis Z, at axle fastener 112 located proximate a first end 114 of crank 102. Proximate second end 116 of crank 102 is attached a pedal axle 118 for attaching a pedal (not shown). A rider applies force represented by arrow 120 to the pedal thereby causing crank 100 to rotate about lateral axis Z at the bottom bracket (not shown).

As the rider applies force 120, the torque causes bending in the crank 100 which is measured by first and second strain gauges 122, 124. First strain gauge 122 is located on top surface 104, and second strain gauge 124 is located on bottom surface 106 of crank 100 (and thus depicted in dashed lines). First and second strain gauges 122, 124 are wired via circuitry (not shown) into a Wheatstone bridge. The configuration of first and second strain gauges 122, 124 allows sensitivity to bending of crank 100 as force 120 is applied to the pedal, but insensitivity to axial forces applied along the longitudinal axis X. However, first and second strain gauges are very susceptible to physical damage because they are located on the top and bottom surfaces 104, 106 and are frequently in physical contact with the rider and other elements. Moreover, having the first and second gauges 104, 106 located on opposing surfaces of crank 100 makes manufacturing difficult and inefficient.

SUMMARY

In one embodiment, a crank power measurement system measures one or more of force, torque, power, and velocity of the crank. The system includes a crank, two or more strain gauges located on a surface of the crank, and electronics for receiving strain data from the two or more strain gauges and determining at least one or more of bend-strain, shear-strain, and axial strain.

In another embodiment, a bicycle crank mounted power generator for generating power when the bicycle is being ridden by a user. The bicycle crank mounted power generator including a base ring fixedly attached to a frame of the bicycle, the base ring circling a bottom bracket attached to a crank, a plurality of magnets coupled with the base ring, a coil system attached to the crank located adjacent to the plurality of magnets such that when the crank rotates about the bottom bracket, the coil generates an output at leads of the coil, and electronics configured to manipulate the output to at least one of power an electronic device or store the output in a power supply.

DETAILED DESCRIPTION OF THE EMBODIMENTS

Figure 1:
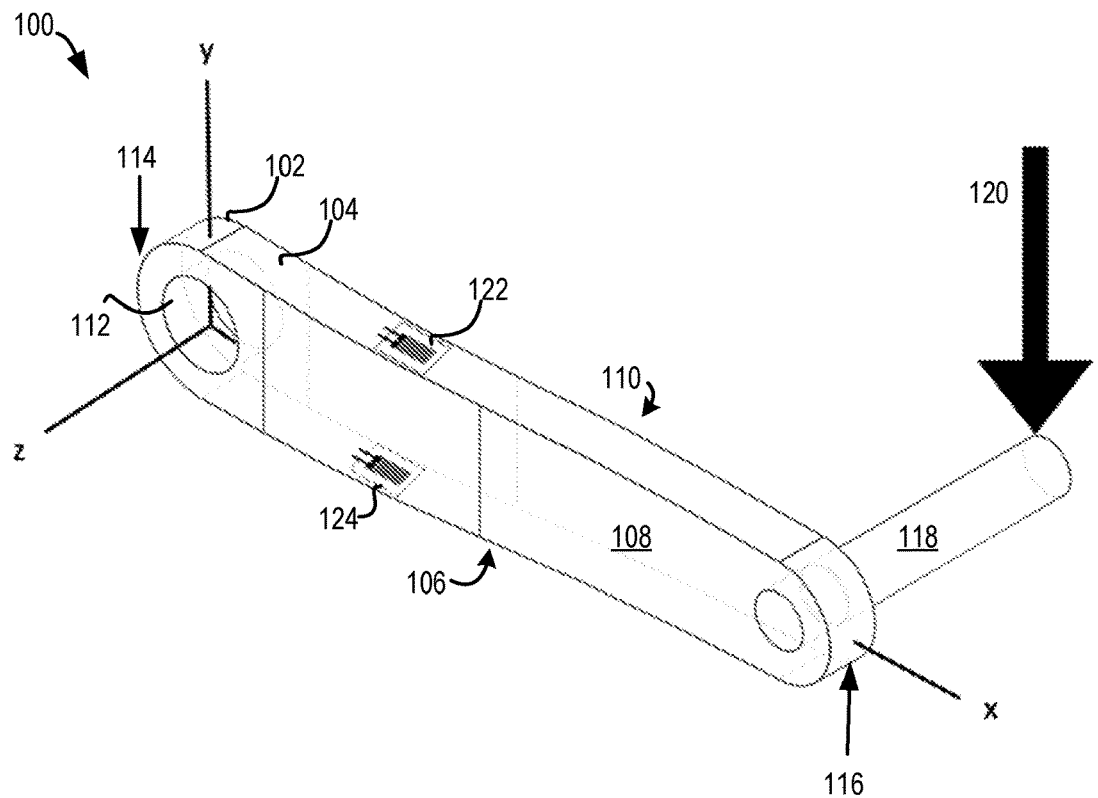
FIG. 1 depicts a prior art bicycle pedal-crank for measuring torque being produced by the pedal force in the crank's rotation plane.

Certain embodiments disclosed herein relate to a body instrumented with strain sensors to indirectly measure loads applied to the body. In a typical use case, it is desired to determine the applied forces or moments along a specified axis. To enable this measurement, one or more strain sensors are affixed to the body. Known loads are applied to the body and the strains are recorded to enable calibration of sensors to these loads. For regular geometries, homogeneous materials and well defined load cases, it is possible to apply only one primary strain sensor to enable accurate, repeatable measurements. In most situations however, several strain sensors must be applied to augment the primary strain sensor to correct for such things such as irregular geometries, variations in manufacturing, off-axis loading and non-ideal sensor placements, to name a few.

Calibration of various strain sensors may include attaching a single weight in one orientation and observing the strain output(s), or it may involve several weights applied to the body in various positions and orientations. This data can then be processed with sophisticated models that include regression.

The strain sensing is typically carried out with a strain gauge. A single gauge may be used to measure the strain in a particular orientation, but two, three, four or more gauges may be combined into a Wheatstone bridge to measure the strain response in a single direction. Any form of Wheatstone bridge, including quarter, half, three-quarter or full Wheatstone bridge may be utilized without departing from the scope hereof. Additional gauges have several benefits, such as to provide increased sensitivity—in some cases up to four times the sensitivity of a single gauge. Another benefit for additional gauges is that temperature changes in the metal cause the material to expand or contract, which is measured as a change in strain even though no loads have been applied. Where multiple gauges are configured in a Wheatstone bridge, they become less temperature sensitive.

Even when strain sensing gauges are wired into a Wheatstone bridge, temperature sensitivity may still be exhibited due to zero load offset changes and sensitivity slope changes in the output. Due to individual characteristics of the gauges, circuitry and enclosure, the zero offset changes may be individually tested. It may be possible to model these offset effects with a simple linear change over a small range in temperatures, thus only requiring a two-point temperature calibration. However, in the more general case, a multi-point temperature characterization may be conducted for a non-linear variation in zero load offset versus temperature. The same discussion can also be carried out for the change in slope sensitivity with respect to temperature. Each configuration may be tested over several different temperatures for a full non-linear mapping of the response option. In the simplest case, a simple two-point temperature test may be sufficient for example, when a global structural stiffness property is the dominant factor in the slope change.

Figure 2:
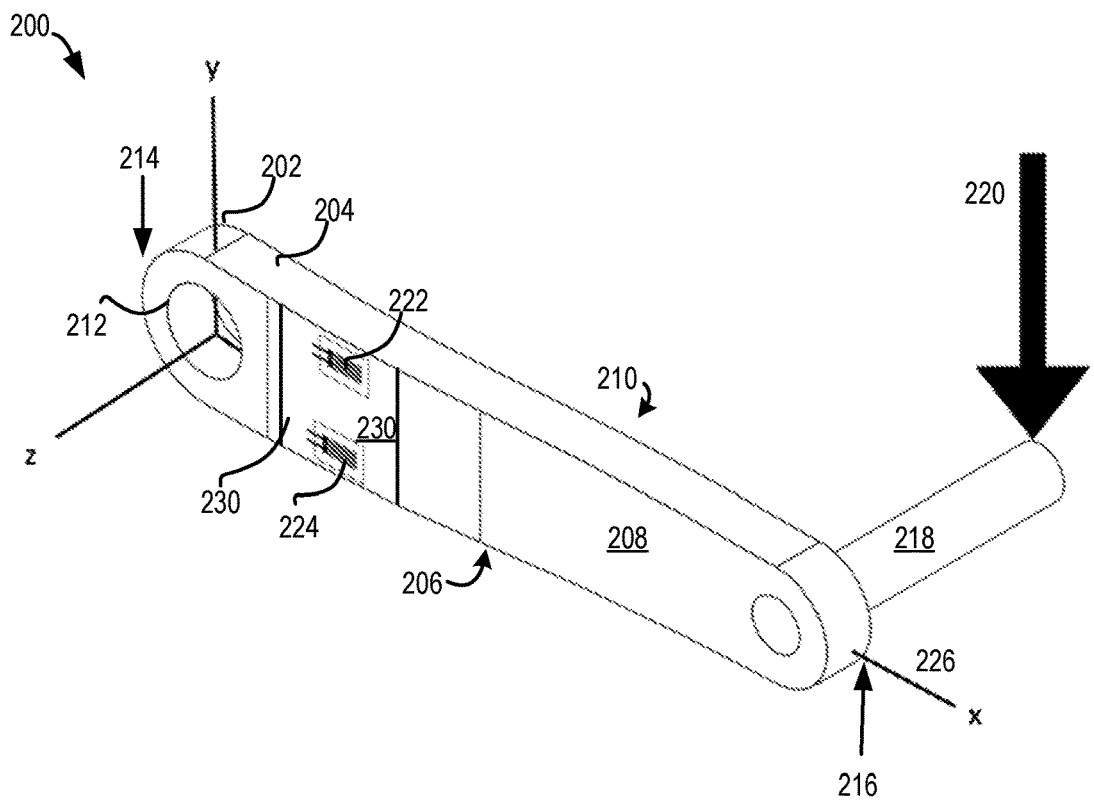
FIG. 2 depicts an exemplary crank having inner surface strain gauges, in one embodiment.

FIG. 2 depicts an exemplary crank assembly 200 having inner surface strain gauges, in one embodiment. Crank assembly 200 includes a crank 202, having a longitudinal axis X, a vertical axis Y, and a lateral axis Z. Crank 202 has a top surface 204, a bottom surface 206, an inner surface 208, and an outer surface 210. Crank assembly 200 has first and second bend-sensing strain gauges 222, 224 located on the inner surface 208, with respect to crank assembly 200 positioned on a bicycle, of crank 202. Crank 202 attaches to a bottom bracket (not shown), that corresponds to lateral axis Z, at axle fastener 212 located proximate a first end 214 of crank 202. Proximate second end 216 of crank 202 is attached a pedal axle 218 for attaching a pedal (not shown). A rider applies force in the direction shown by arrow 220 to the pedal thereby applying force along vertical axis Y (and potentially longitudinal axis X) causing crank assembly 200 to rotate about lateral axis Z at the bottom bracket. It should be appreciated that the actual force on crank 202 is not limited to vertical force as shown by arrow 220, but in reality includes forces in multiple dimensions including the X, Y, and Z axes. Arrow 220 is for illustrative purposes only.

As the rider applies force 220, the torque causes bending in the crank assembly 200 which is measured by first and second bend-sensing strain gauges 222, 224. First strain gauge 222 is located on inner surface 108, above the neutral axis 226 of the crank assembly 200. Second strain gauge 224 is located on the inner surface 108 of crank assembly 200 located below the neutral axis of the crank assembly 200. First and second bend-sensing strain gauges 222, 224 are wired via circuitry (not shown) into a Wheatstone bridge such that they are insensitive to axial forces (e.g., around the X axis/neutral axis 226) but remain sensitive to bending (along the X axis/neutral axis 226). The circuitry and electronics associated with first and second bend-sensing strain gauges 222, 224 are discussed in further detail below. Placing the bend-sensing strain gauges 222, 224 on the inner surface 208 of crank assembly 200 provides significantly increased protection of the gauges because they are less susceptible to contact by the rider or other elements.

In FIG. 2, neutral axis 226 is indicated the same as longitudinal axis X. For a completely symmetrical crank assembly 200, the neutral axis 226 is along the geometric center (longitudinal axis X), whereas in other geometries, this must be experimentally or analytically determined. For maximum bend sensing, first and second bend-sensing gauges 222, 224 are located farther away from neutral axis 226.

Figure 3:
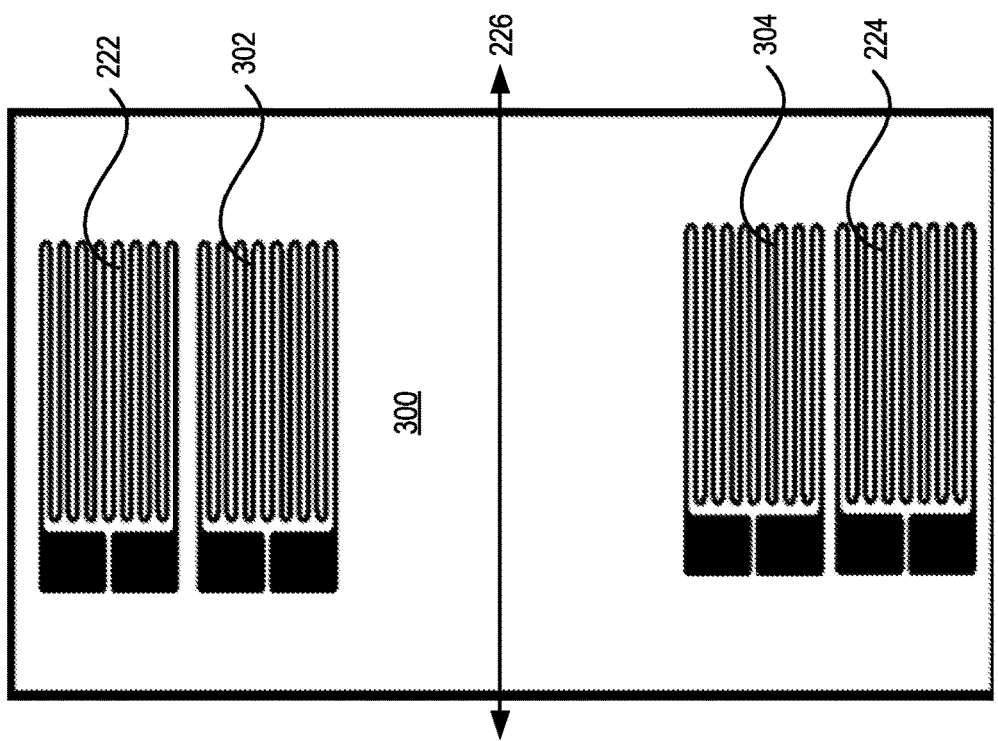
FIG. 3 depicts an additional strain gauge configuration for use with the crank of FIG. 2, in one embodiment.

Additional strain gauges may be added to increase the sensitivity of the system. For example, FIG. 3 depicts an additional strain gauge configuration 300 for use with crank assembly 200 of FIG. 2, in one embodiment. Strain gauge configuration 300 attaches to crank assembly 200 in the same location 230 (referring to FIG. 2) and orientation as first and second bend-sensing strain gauges 222, 224 of FIG. 2. Strain gauge configuration 300 includes first and second bend-sensing strain gauges 222, 224, as discussed above with respect to FIG. 2, as well as third and fourth bend-sensing strain gauges 302, 304. Third bend-sensing strain gauge 302 is located between first bend-sensing strain gauge 222 and neutral axis 226. Fourth bend-sensing strain gauge 304 is located between second bend-sensing strain gauge 224 and neutral axis 226.

Figure 4:
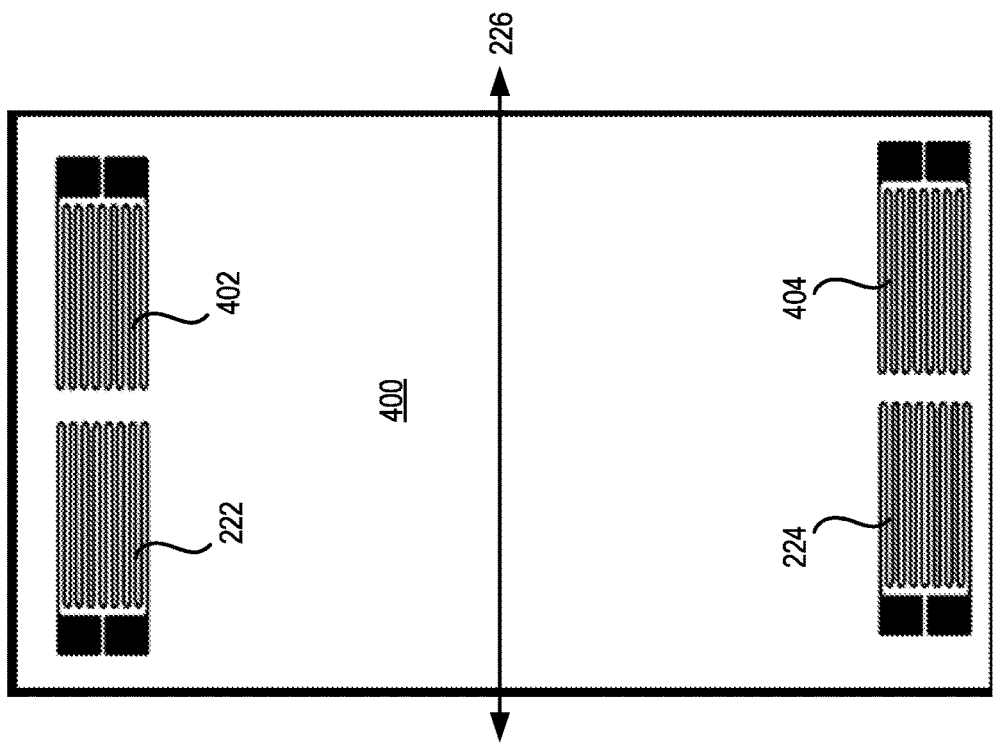
FIG. 4 depicts an additional strain gauge configuration for use with the crank of FIG. 2, in one embodiment.

FIG. 4 depicts an additional strain gauge configuration 400 for use with crank assembly 200 of FIG. 2, in one embodiment. Strain gauge configuration 400 attaches to crank assembly 200 in the same location 230 (referring to FIG. 2) and orientation as first and second bend-sensing strain gauges 222, 224 of FIG. 2. Strain gauge configuration 400 includes first and second bend-sensing strain gauges 222, 224, as discussed above with respect to FIG. 2, as well as third and fourth bend-sensing strain gauges 402, 404. Third bend-sensing strain gauge 402 is located adjacent to, and symmetrically opposed to, first bend-sensing strain gauge 222 at the same distance from neutral axis 226. Fourth bend-sensing strain gauge 404 is located adjacent to, and symmetrically opposed to, second bend-sensing strain gauge 224 at the same distance from neutral axis 226. Configurations 300 and 400 increase the sensitivity of the sensed strain detected by the strain gauges.

Figure 5:
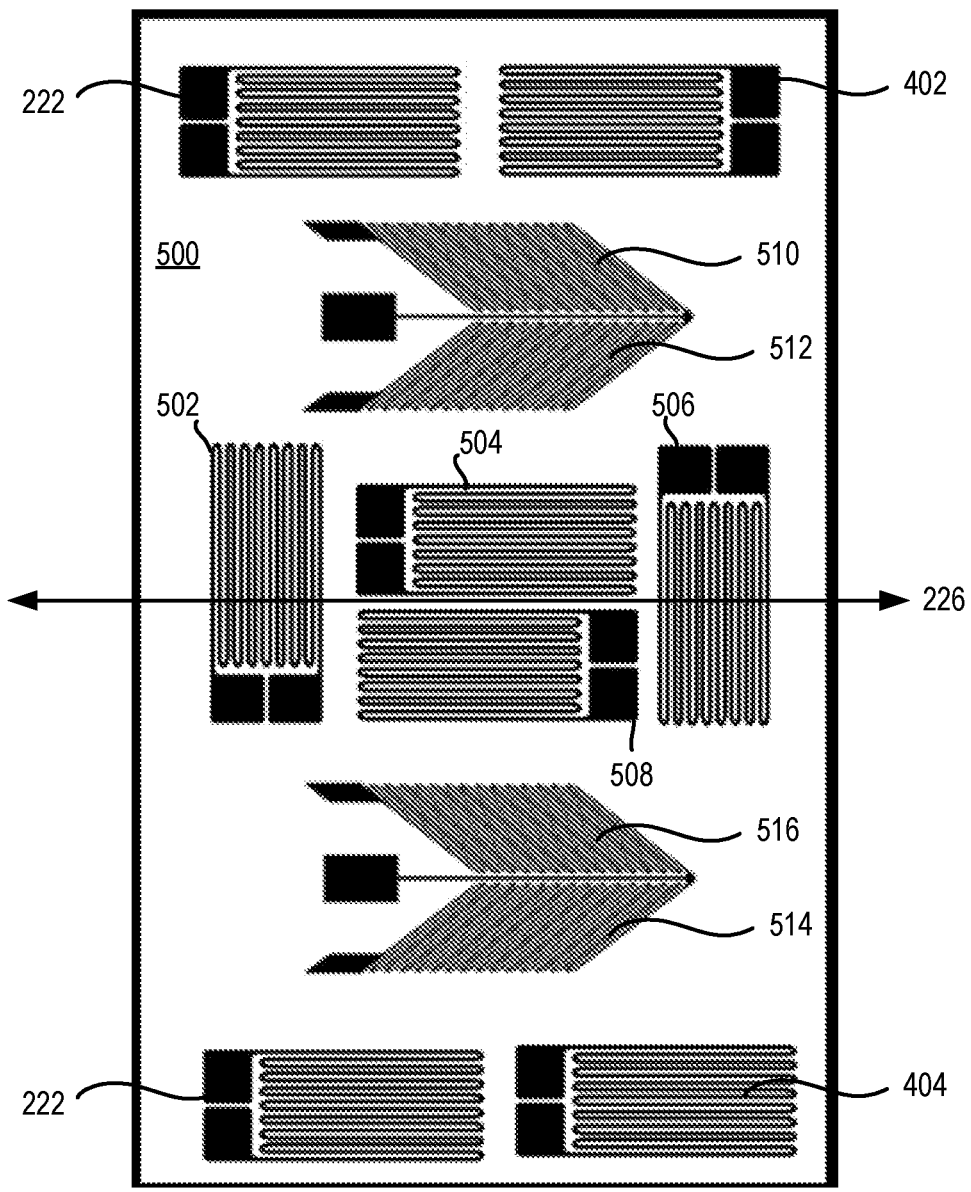
FIG. 5 depicts an additional strain gauge configuration for use with the crank assembly of FIG. 2, in one embodiment.

Using additional shear- and/or axial-sensing strain gauges allows compensation for asymmetries, non-design loads, and imperfections in manufacturing (e.g., of the crank assembly 200 and/or gauges 222, 224, 302, 304, 402, 404) based upon additional data obtained by the shear- and axial-sensing strain gauges. Configurations 300 and 400 are set up such that first, second, third and fourth bend-sensing strain gauges are coupled in a full-Wheatstone bridge, or two half-Wheatstone bridges FIG. 5 depicts an additional strain gauge configuration 500 for use with crank assembly 200 of FIG. 2, in one embodiment. Strain gauge configuration 500 attaches to crank assembly 200 in the same location 230 (referring to FIG. 2) and orientation as first and second bend-sensing strain gauges 222, 224 of FIG. 2. Strain gauge configuration 500 includes first and second bend-sensing strain gauges 222, 224, as discussed above with respect to FIG. 2. Strain gauge configuration 500 also includes third and fourth bend-sensing strain gauges 402, 404, as discussed above with respect to FIG. 4. First, second, third, and fourth bend-sensing strain gauges 222, 224, 402, 404 may be coupled together in a first full-Wheatstone bridge, or first and second half-Wheatstone bridges.

Strain gauge configuration 500 also includes first, second, third, and fourth axial-sensing strain gauges 502, 504. 506, 508. Second axial-sensing strain gauge 504 is rotated 90 degrees with respect to first axial-sensing strain gauge 502. Third axial-sensing strain gauge 506 is rotated 90 degrees with respect to second axial-sensing strain gauge 504, and 180 degrees with respect to first axial-sensing strain gauge 502. Fourth axial-sensing strain gauge 508 is rotated 90 degrees with respect to third axial-sensing strain gauge 506, 180 degrees with respect to second axial-sensing strain gauge 504, and 270 degrees with respect to first axial-sensing strain gauge 502. In general, two of the axial-sensing strain gauges are horizontally oriented along the longitudinal axis Z, and two of the axial sensing strain gauges are vertically oriented. First, second, third, and fourth axial-sensing strain gauges 502, 504, 506, 508 are located along neutral axis 226 and may be coupled together in a second full-Wheatstone bridge, or third and fourth half-Wheatstone bridges.

Strain gauge configuration 500 also includes first, second, third, and fourth shear-sensing strain gauges 510, 512, 514, 516. Shear-sensing gauges are most sensitive to torsion of crank 202, or in other words twisting of crank 200 about the X axis. First shear-sensing strain gauge 510 is located between first and third bend-sensing strain gauges 222, 402 and second shear-sensing strain gauge 512. Second shear-sensing strain gauge 512 is located between first shear-sensing strain gauge 510 and neutral axis 226. Second shear-sensing strain gauge 512 may be oriented such that it is mirrored vertically with respect to first shear-sensing strain gauge 510. Third shear-sensing strain gauge 514 is located between second and fourth bend-sensing strain gauges 224, 404 and fourth shear-sensing strain gauge 516. Fourth shear-sensing strain gauge 516 is located between third shear-sensing strain gauge 514 and neutral axis 226. Fourth shear-sensing strain gauge 516 may be oriented such that it is mirrored vertically with respect to third shear-sensing strain gauge 514 and in the same orientation as second shear-sensing strain gauge 512. First, second, third and fourth shear-sensing strain gauges 510, 512, 514, and 516 may be coupled together in a third full-Wheatstone bridge, or fifth and sixth half-Wheatstone bridges.

Figure 6A:
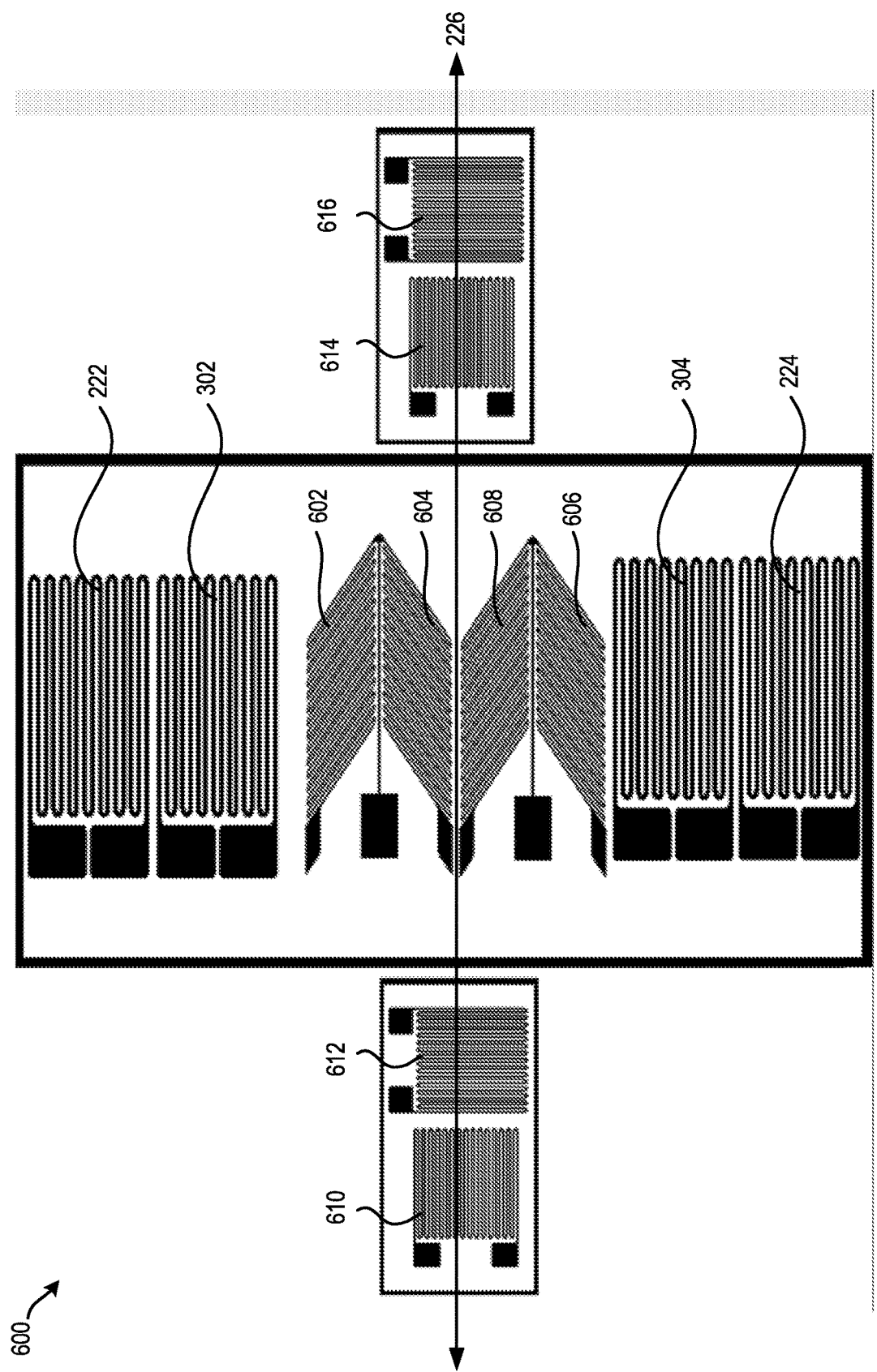
FIGS. 6A-C depict additional strain gauge configurations for use with the crank assembly of FIG. 2, in alternate embodiments.
Figure 6B:
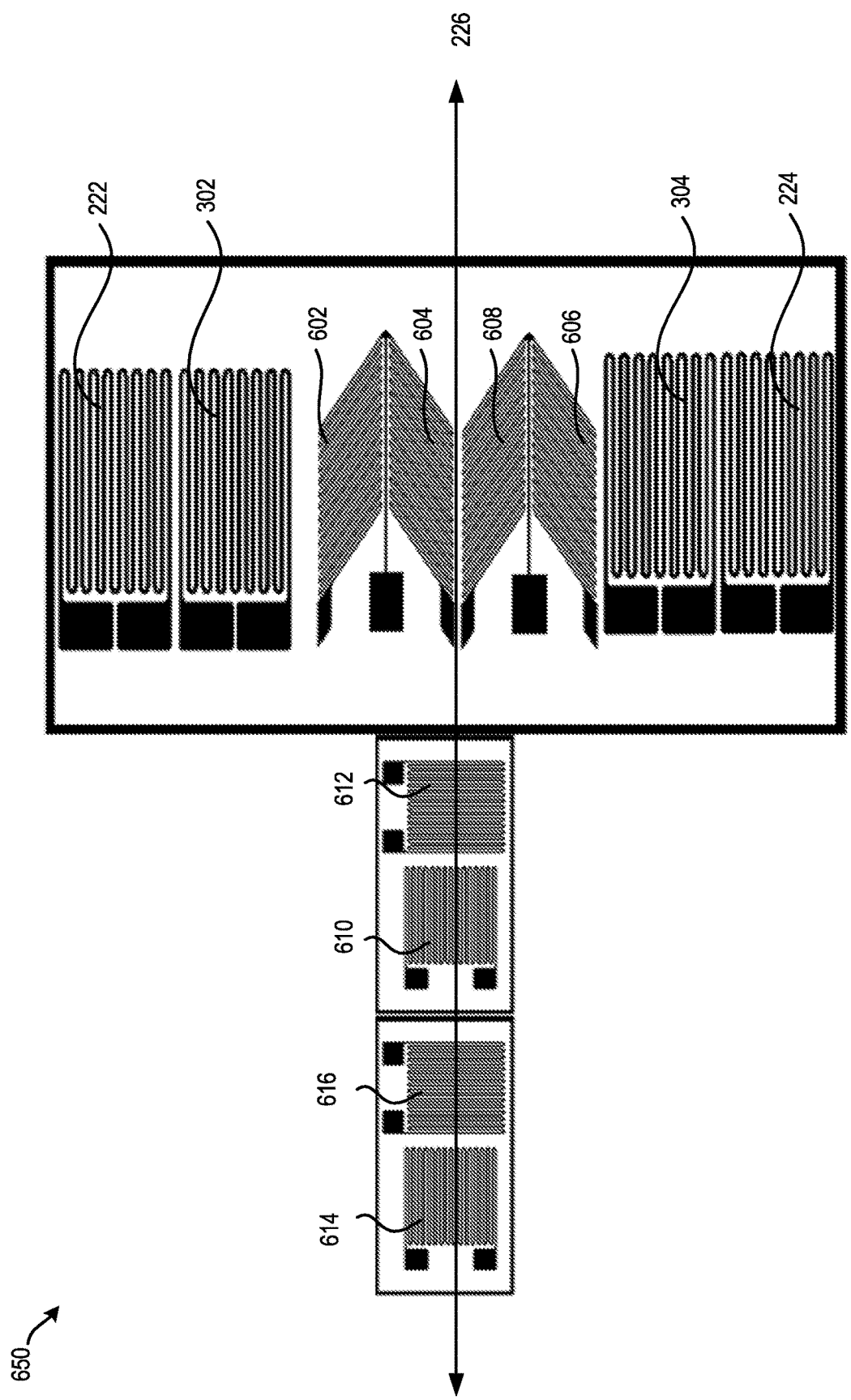
Figure 6C:
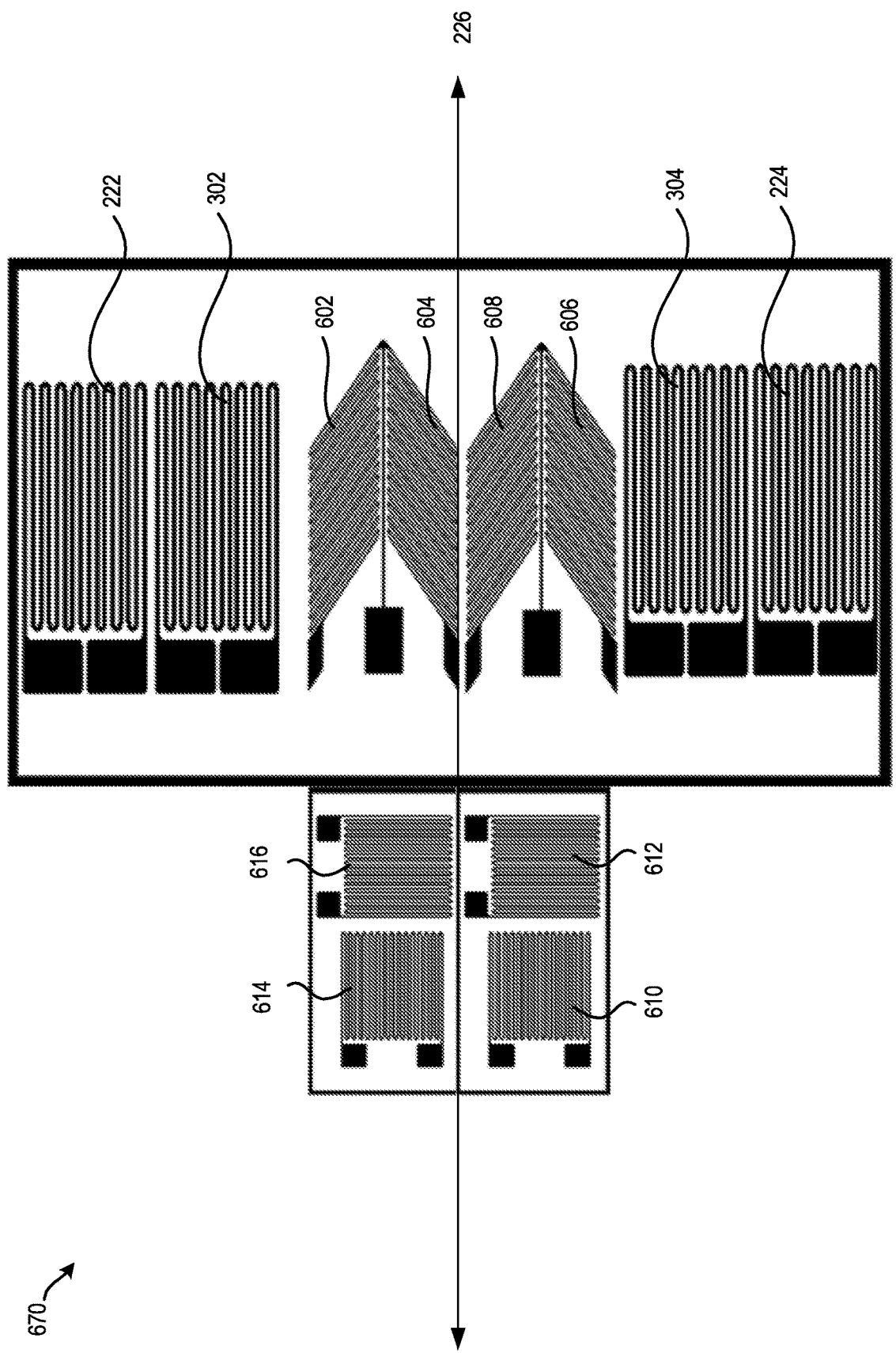

FIGS. 6A-C depict additional strain gauge configurations 600, 650, 670 for use with crank assembly 200 of FIG. 2, in alternate embodiments. Strain gauge configurations 600, 650, 670 attach to crank assembly 200 in the same location 230 (referring to FIG. 2) and orientation as first and second bend-sensing strain gauges 222, 224 of FIG. 2. Strain gauge configurations 600, 650, 670 include first and second bend-sensing strain gauges 222, 224, as discussed above with respect to FIG. 2. Strain gauge configurations 600, 650, 670 include third and fourth bend-sensing strain gauges 302, 304, as discussed above with respect to FIG. 3. First, second, third, and fourth bend-sensing strain gauges 222, 224, 302, 304 may be coupled together in a first full-Wheatstone bridge, or first and second half-Wheatstone bridges.

Strain gauge configurations 600, 650, 670 also include first, second, third, and fourth shear-sensing strain gauges 602, 604, 606, 608. First shear-sensing strain gauge 602 is located between third bend-sensing strain gauge 302 and second shear-sensing strain gauge 604. Second shear-sensing strain gauge 604 is located between first shear-sensing strain gauge 602 and neutral axis 226. Second shear-sensing strain gauge 604 may be oriented such that it is mirrored vertically with respect to first shear-sensing strain gauge 602. Third shear-sensing strain gauge 606 is located between fourth bend-sensing strain gauges 304 and fourth shear-sensing strain gauge 608. Fourth shear-sensing strain gauge 608 is located between third shear-sensing strain gauge 606 and neutral axis 226. Fourth shear-sensing strain gauge 608 may be oriented such that it is mirrored vertically with respect to third shear-sensing strain gauge 606 and in the same orientation as second shear-sensing strain gauge 604. First, second, third and fourth shear-sensing strain gauges 602, 604, 606, 608 may be coupled together in a second full-Wheatstone bridge, or third and fourth half-Wheatstone bridges.

Strain gauge configuration 600 also includes first, second, third, and fourth axial-sensing strain gauges 610, 612, 614, 616. First and second axial-sensing strain gauges 610, 612 are located along neutral axis 226 offset, towards the bottom bracket, from the bend-sensing and shear sensing strain gauges. Third and fourth axial-sensing strain gauges 614, 616 are located along neutral axis 226 offset, away from the bottom bracket, from the bend-sensing and shear sensing strain gauges. Second axial-sensing strain gauge 614 may be rotated 90 degrees with respect to first axial-sensing strain gauge 610. Third axial-sensing strain gauge 614 may be rotated 90 degrees with respect to fourth axial-sensing strain gauge 616. In general, two of the axial-sensing strain gauges are horizontally oriented along the longitudinal axis Z, and two of the axial sensing strain gauges are vertically oriented. First, second, third, and fourth axial-sensing strain gauges 610, 612, 614, 616 may be coupled together in a third full-Wheatstone bridge, or fifth and sixth half-Wheatstone bridges.

Strain gauge configuration 650 is similar to strain gauge 600, however each of first, second, third, and fourth axial-sensing strain gauges 610, 612, 614, 616 are located along neutral axis 226 and offset towards the bottom bracket. Strain gauge configuration 670 is also similar to strain gauge 600, however each of first, second, third and fourth axial-sensing strain gauges 610, 612, 614, 616 are located offset from neutral axis 226 and offset towards the bottom bracket. It should be appreciated that strain gauge configuration 670 could be modified such that the axial-sensing strain gauges are offset from the natural axis and away from the bottom bracket as well.

Figure 7:
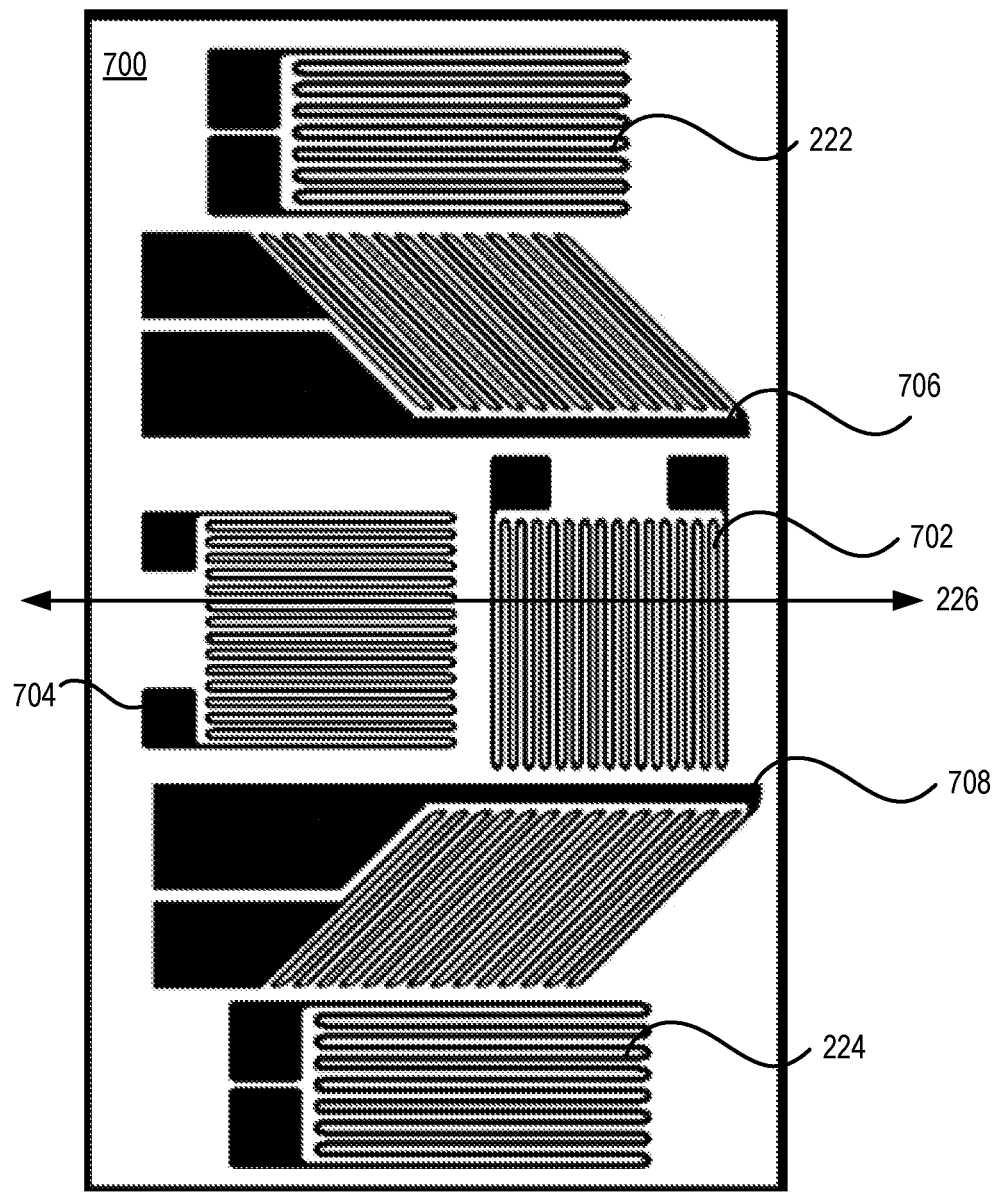
FIG. 7 depicts an additional strain gauge configuration for use with the crank assembly of FIG. 2, in one embodiment.

FIG. 7 depicts an additional strain gauge configuration 700 for use with crank assembly 200 of FIG. 2, in one embodiment. Strain gauge configuration 700 attaches to crank assembly 200 in the location 230 (referring to FIG. 2) and orientation as first and second bend-sensing strain gauges 222, 224 of FIG. 2. Strain gauge configuration 700 includes first and second bend-sensing strain gauges 222, 224, as discussed above with respect to FIG. 2, which may be coupled together in a first half-Wheatstone bridge.

Strain gauge configuration 700 includes first and second axial-sensing strain gauges 702, 704. Second axial-sensing strain gauge 704 is rotated 90 degrees with respect to first axial-sensing strain gauge 702. First and second axial-sensing strain gauges 702, 704 are located along neutral axis 226 and may be coupled together in a second half Wheatstone bridge.

Strain gauge configuration 700 also includes first and second shear-sensing strain gauges 706, 708. First shear-sensing strain gauge 706 is located between first bend-sensing strain gauge 222 and neutral axis 226. Second shear-sensing strain gauge 708 may be oriented such that it is mirrored vertically with respect to first shear-sensing strain gauge 706. Second shear-sensing strain gauge 708 is located between second bend-sensing strain gauge 224 and neutral axis 226. First and second shear-sensing strain gauges 706, 708 may be coupled together in a third half Wheatstone bridge.

A duplicate of configuration 700 may be placed adjacent to configuration 700 thereby resulting in four of each of the bend-, shear-, and axial-sensing strain gauges. In such an embodiment, the bend-, shear-, and axial-sensing strain gauges may be coupled together in respective first, second, and third full-Wheatstone bridges.

In each of configuration 300-700, a calibration procedure may be carried out with variety of known loads to determine how each gauge set responds to these loads. Then, when real-life pedal forces are applied to the crank, it is possible to determine the loads of interest. These loads of interest are typically the moment causing corresponding to the bike's input power, as well the axial load and direction acting on the pedal as the crank rotates.

In a cycling application, the loads applied to the crank are due to loads being applied to the pedals. By the very nature of the pedal and crank design, these applied forces are offset from the crank and thus do not produce a pure bending moment about the longitudinal axis Z of the crank assembly 200. Instead, this pedal offset causes several simultaneous applied loads that include, but are not limited to bending, torsion and axial loads. This is further compounded by the fact that individual cyclists have their own applied force profile as their legs move to produce a crank revolution. In general, the applied pedal forces aren't perpendicular to the crank and they may include axial and torsional components as well. The purpose of the multi-gauge sensors and the calibration is to separate these loads so that the bending moment of interest, axial forces and pedal offsets are accurately estimated.

In the above discussion of FIGS. 2-7, it should be appreciated that more or fewer strain gauges may be implemented, in additional configurations without departing from the scope hereof Where the figures depict a given strain gauge, it should be understood that each individual depiction may represent a single strain gauge, or a pair of strain gauges joined together, or more than two strain gauges joined together without departing from the scope hereof. Moreover, where a given strain gauge is depicted on the neutral axis 226, it should be appreciated that such strain gauge may also be offset from the neutral axis 226 without departing from the scope hereof. Further, where a given strain gauge is depicted offset from the neutral axis 226, it should be appreciated that such strain gauge may also be located on the neutral axis 226 without departing from the scope hereof. Utilizing such configurations allows for one set of strain gauges to be a primary set of strain gauges. Secondary set(s) of strain gauges may then be utilized to augment the accuracy of the primary set. For example, the primary set may be any of the bend-sensing strain gauges discussed above, with the secondary set being any of the shear- or axial-sensing strain gauge sets. This combination allows for increased accuracy and efficiency while accommodating any variable, such as shape, size temperature, of crank assembly 200.

Temperature Compensation:

Varying temperatures affect several aspects of strain gages differently based on gage materials and backings. These fall into the categories of zero offset shift, changes in the gage factor (the electrical response compared to the mechanical response) sensitivity, and change in material properties at temperature. For passively compensated sensing such as half bridges, full bridges, or other expansions that are passively compensated, the thermal error is a combination of changes in lead wire resistance and variance in the thermal response of the gage. As such by taking a minimum of two data points it is possible to linearly regress a zero offset shift versus temperature. For single gages which have a non-linear temperature response this method is expanded to include a non-linear regression to appropriately match. During operation, temperature measurements of the gage or the underlying material can be made and using the regression the zero offset may be compensated for.

If the crank is made from high thermally conductive materials, like aluminum, it is possible to take a temperature reading at a nearby site and assume that all gages are this temperature. For materials with low thermal conductivity, like carbon, measurements at the gage sites may be required and the same method of compensation can be used.

The strains measured may include one or all of bend, axial and shear, and may be multiplied by coefficients and then added together to determine the applied torque. These coefficients may be determined from calibration. A different calibration procedure is used to determine different coefficients that may be used to determine the applied axial forces or other load of interest. These coefficients are slightly sensitive to temperature. To determine their sensitivity to temperature, calibrations can be performed at different temperatures. For example, a calibration could be performed at room temperature and then in an oven and/or in a freezer.

A change in temperature can also affect the calibration values by modifying the gauge factor response or the modulus of a material. It is possible to compensate via linear or non-linear means by combining these two effects and measuring the response to calibration at various temperatures. This results in changes to the calibration factors that can be interpolated during operation in order to increase accuracy.

Accordingly, in addition to each of the above discussed strain gauges, crank assembly 200 may further include one or more temperature sensors. A single temperature sensor may be used in high thermally conductive materials. Alternatively, multiple temperature sensors may be used such that a temperature sensor is located next to each of, or a group of, the strain gauges discussed in FIGS. 2-7, above.

Figure 8:
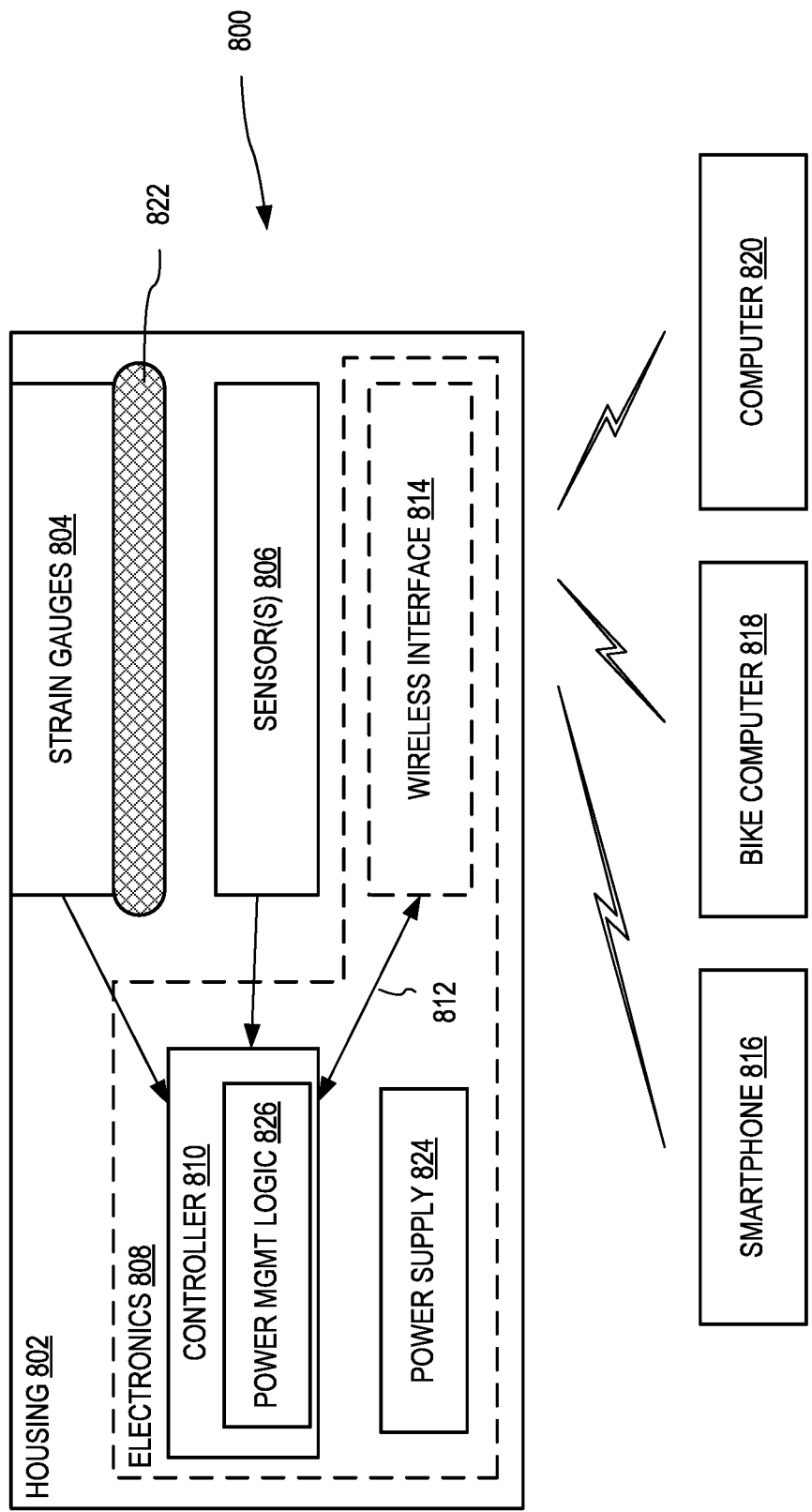
FIG. 8 depicts an exemplary strain gauge electronics module 800, in one embodiment.

Electronics Module for Use with Strain Gauges:

FIG. 8 depicts an exemplary strain gauge electronics module 800, in one embodiment. Strain gauge electronics module 800 includes a housing 802 housing strain gauges 804, additional sensors 806, and electronics 808.

Housing 802 may be permanently installed onto a crank (e.g. crank assembly 200 of FIG. 2). Alternatively, housing 802 may be a part of an aftermarket device and be installed using the installation methods of, and include one or more features of, the housing discussed in PCT/IB2015/002099 with respect to housing 302 and installation features thereof.

The strain gauges 804 may include any of the strain gauge configurations discussed above with regards to FIGS. 2-7, or any other configuration of strain gauges. Strain gauges 804 are coupled to controller 810 of electronics 808. Controller 810 may operate to control operation of strain gauges 804, and also communicate power readings 812 to a rider. Power readings 812 may be based on the data obtained from strain gauges 804 and optionally sensors 806, to a rider. In one example of operation, power readings 812 are transmitted via a wireless interface 814 to one or more of a smart phone 816, bike computer 818, or computer 820. Power readings 812 may also be sent over hardwired communication lines as well. Strain gauges 804 may be incorporated with housing 802, or may be located exterior thereto and attached to the crank at a different location. For example, the strain gauges 804 may be built into the crank, and housing 802 may be attached thereafter and electrically coupled to strain gauge leads once installed.

Strain gauges 804 may, in certain embodiments, include a thermal conductive pillow (see thermal conductive pillow 822 of FIG. 8) mounted on top thereof (a) to improve measurement of gauge temperatures and corresponding electronic thermal compensation, (b) to improve dissipation of heat generated by strain gauges 102 during measurement, and (c) is used where the printed circuit board assembly has very uniform thermal dissipation characteristics. In an alternative embodiment, a thermally non-conductive pillow may be used to provide thermal isolation of strain gauges 804 to reduce localized thermal gradients from heat sources near the gauges. For example, the thermally non-conductive pillow may be used where a printed circuit board assembly has components that may create large thermal gradients that impact the strain gauges 804. One or more thermal sensors may be positioned on strain gauges 804 to improve temperature measurement accuracy for electronic thermal compensation of measurements. A soft pillow layer may be included to prevent mechanical damage to strain gauges 804 by reducing localized forces on strain gauges 804. For example, clamping forces used during installation may be spread over a larger area by a soft pillow to avoid damage to strain gauges 804.

Additional sensors 806 may include the temperature sensors discussed above, as well as inertial sensors such as those discussed in PCT/IB2015/002099, which is attached hereto as Appendix A. Other sensors than an inertial sensor may be used as well, such as magnetic reed switches or Hall effect sensors to measure angular velocity or cadence. Additional sensors 806 may further include sensor inputs from various sensors utilized by the rider. For example, sensors 806 may include data from aerodynamics, wind, inclination, heart rate, VO2max, etc. so that the efficiency of a cyclist may be determined by controller 810. Such sensor data may be hardwired to housing 802, or may be transmitted wirelessly using wireless interface 814.

Electronics 808 may include the controller 810, as well as a power supply 824 and any other circuitry required to implement the Wheatstone bridges used with strain gauges 804. Power supply 824 may be a battery or other rechargeable power source.

Controller 810 may include power management logic for controlling operation of various devices housed in housing 802. For example, the power management logic 826 may configure the strain gauges 804 according to various frequency sampling rates. During certain phases of the pedaling motion, the recorded strain levels are changing at a very slow rate, thus lower sampling rates may be utilized. During other parts of the pedal stroke however, the gauges may be experiencing rapidly changing loads and thus must be sampled more quickly. This variable sampling rate strategy could also be applied for different cadence rates, different riding styles and different road types.

Alternatively (or in addition to), power management logic 824 may switch on or off one or more of the strain gauges discussed above with respect to FIGS. 2-7 such that only a portion of the strain gauges are operable at a given time. For example, if it is observed that the contribution of one or more sets of gauges (typically the secondary gauges such as the shear-sensing or axial-sensing strain gauges discussed above) are not contributing materially to the output power measurement, these sets of gauges could be turned off. However, in different load applications, these secondary gauges may have significant correctional effects and thus should be included. Another situation occurs whereby not including a certain set of strain gauges sets affects the accuracy by a known factor. This known factor may then be applied as a correction factor and thus the accuracy is preserved while the energy saving is achieved.

Additionally, power management logic 824 may include a learning algorithm whereby repeated patterns in the data produced by strain gauges 804 are recognized. For example, consistent pedal strokes by the rider may provide similar data outputs by the strain gauges 804. Accordingly, the sampling rate of the strain gauges 804, or particular strain gauges 804 which are turned on may be altered to reduce the power used by strain gauges 804 at these repetitive patterns.

Bicycle-Powered Electronics Module:

Power management may be crucial to the life span of the device 800. For example, where electronics module 800 is included on a stationary training bike in a training gym, it may be tedious to frequently change the battery of the power supply 824. Therefore, power supply 824 may be rechargeable using various bicycle powered energy generators. Such bicycle powered energy generators include, but are not limited to: mechanically driven dynamos placed in wheel hubs, axles, bottom bracket of the bicycle frame, pedal spindles; solar panels placed on the rider, or the bicycle frame, or other part of the bicycle; wind generators that capture energy while the rider is moving; or piezo-electric energy supplies attached to the bicycle that creates energy based on bending/stretching of the frame during riding.

Such bicycle powered energy generator could be coupled to the power supply 824 to recharge a rechargeable battery, super capacitor, or other small flywheel capable of storing energy for use within electronics module 800. Such power supply 824 could include a non-rechargeable back-up battery, as well as the rechargeable battery. Furthermore, such power supply 824 could be configured to supply power to other electronic devices on the bicycle, or in use by the user.

Energy generated by such bicycle powered energy generator could be transmitted to the power supply 824 using a variety of methods including, but not limited to, conducting wire, conducting foil, conducting thread, brush contracts to send the power from the bike frame to the crank assembly 200, or wireless methods including non-radiative means such as magnetic inductive coupling, magnetic resonance coupling, capacitive coupling, and radiative far-field wireless using lasers or microwave.

Figure 9:
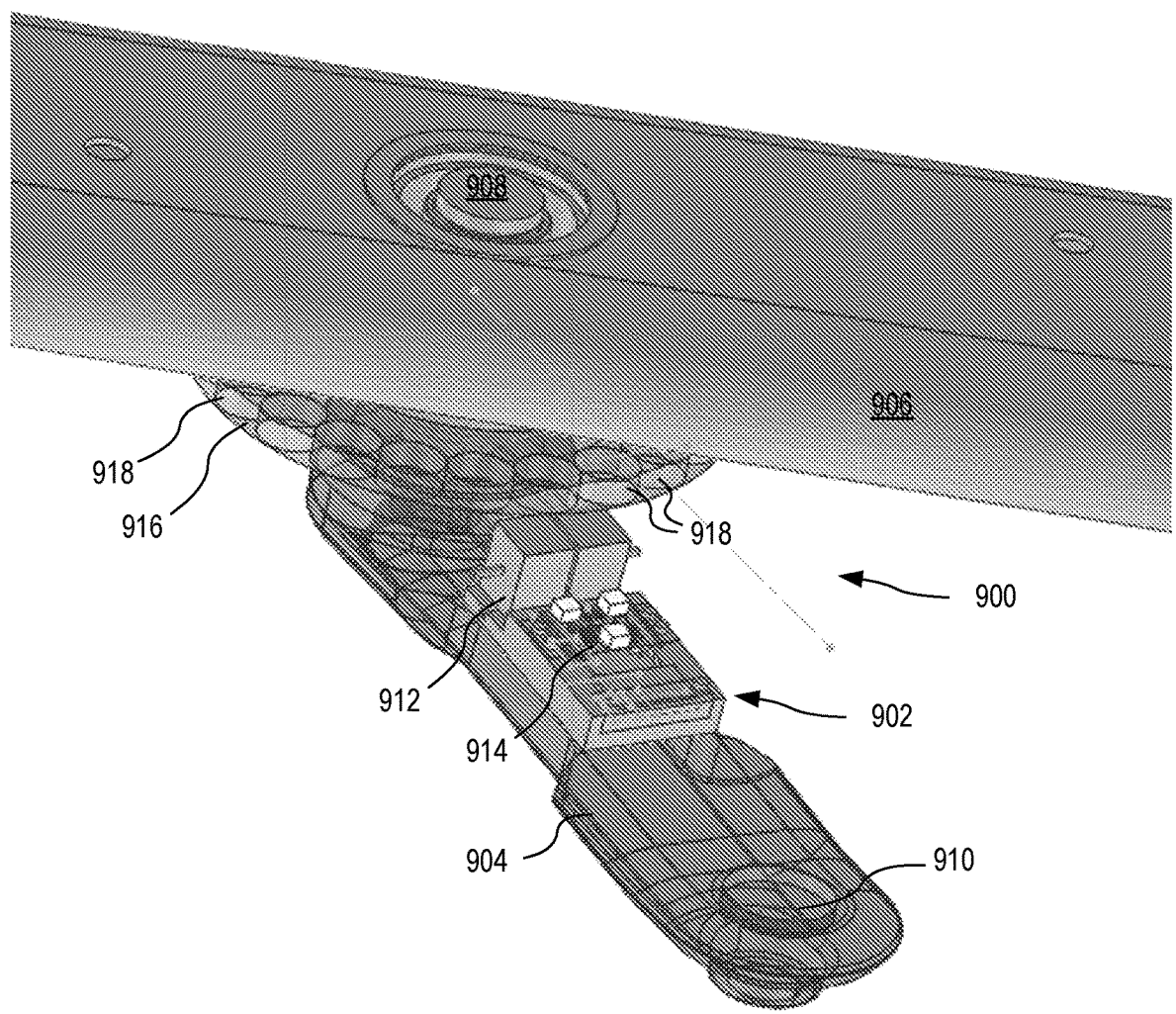
FIG. 9 depicts a bottom perspective view of a bicycle mounted magnetic power generator system, in one embodiment.
Figure 10:
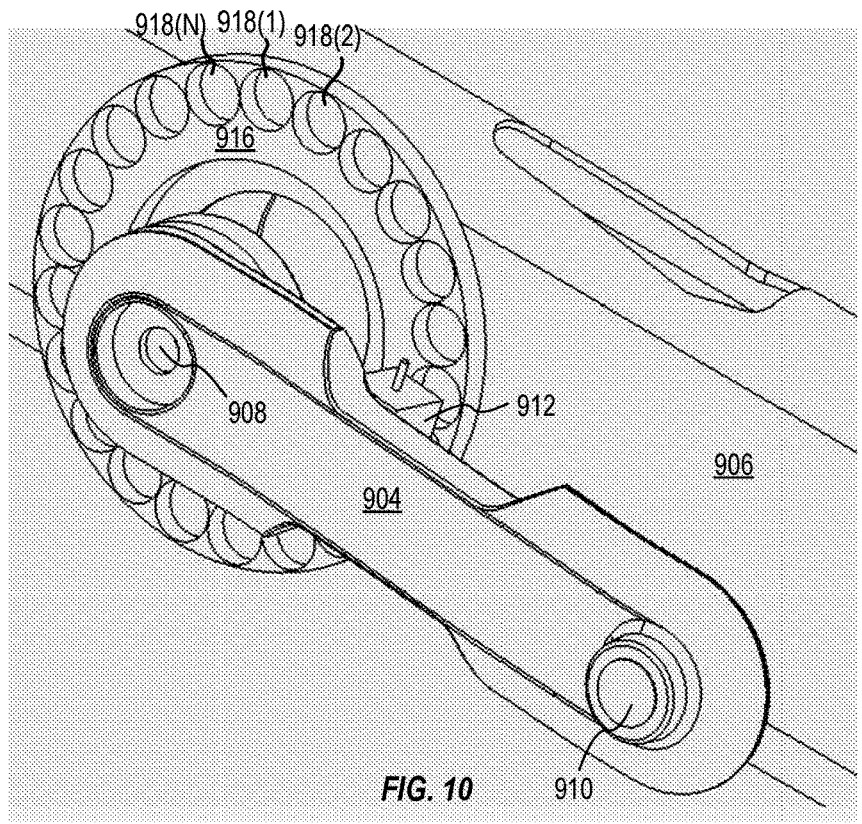
FIG. 10 depicts a top front perspective view of the bicycle mounted magnetic power generator system of FIG. 9.
Figure 11:
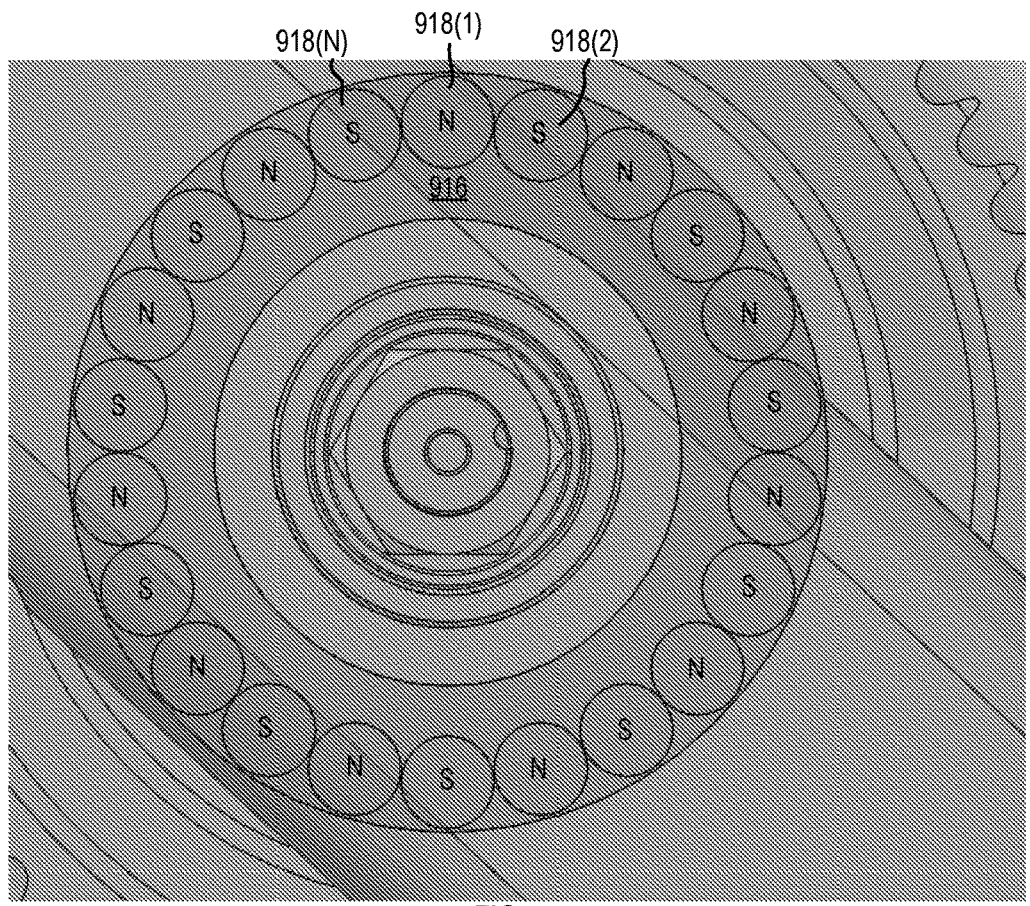
FIG. 11 depicts a front view of the base ring having magnets used in the bicycle mounted magnetic power generator system of FIG. 9, in one embodiment.
Figure 12A:
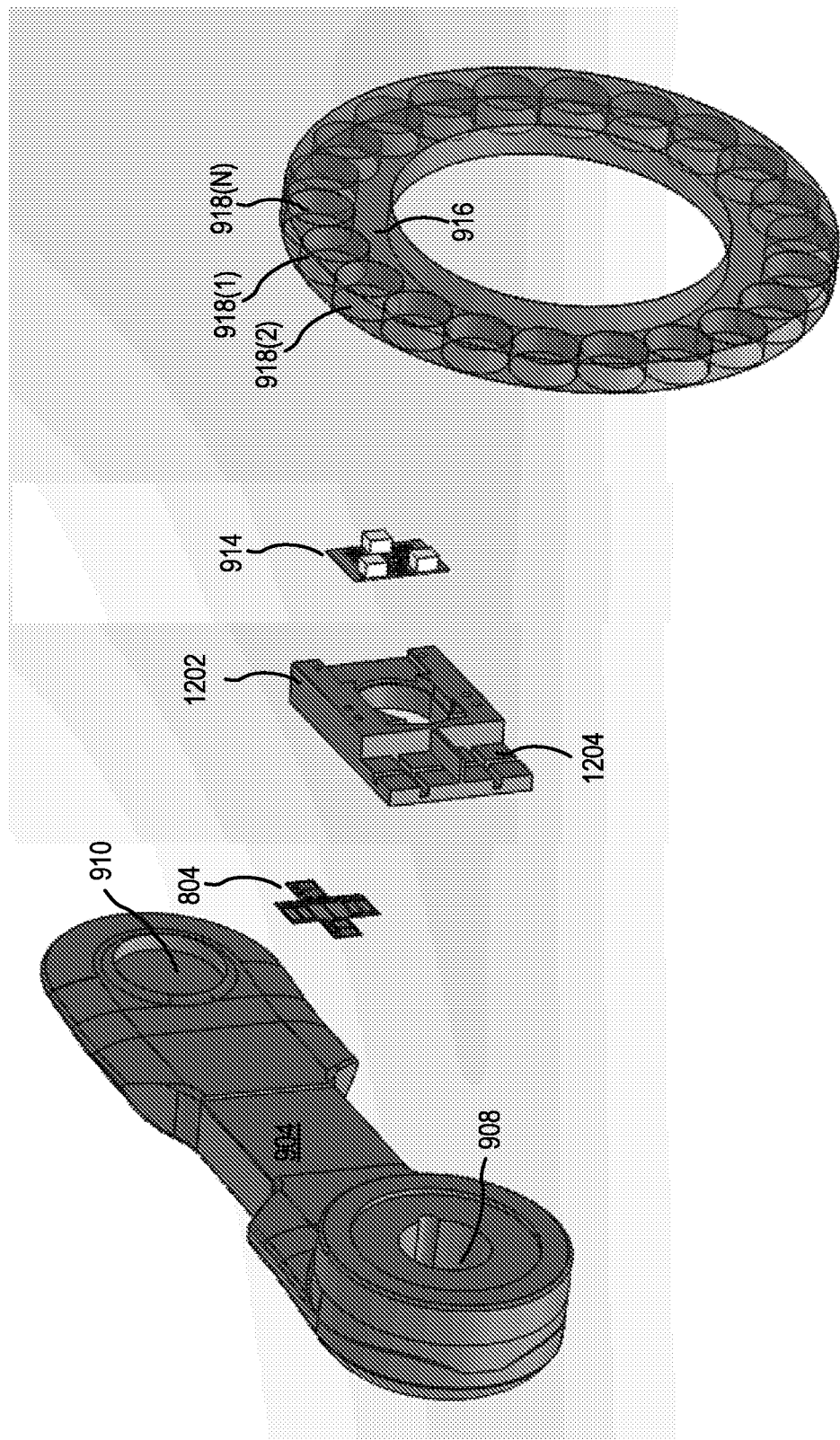
FIG. 12A depicts an exploded view of the bicycle mounted magnetic power generator system of FIG. 9.
Figure 12B:
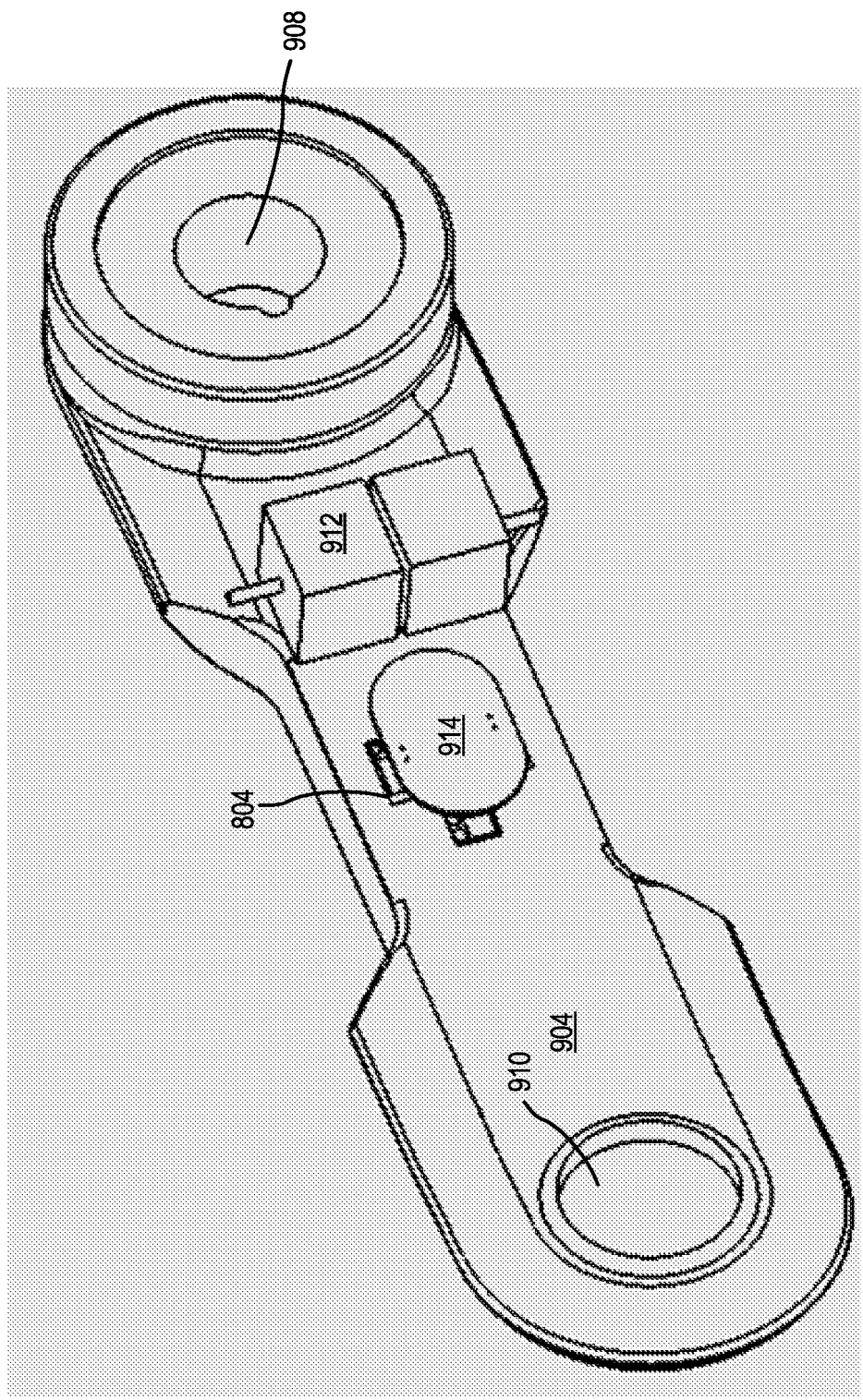
FIG. 12B depicts the strain gauges, electronics, and coil when mounted on the bicycle mounted magnetic power generator system, without the base portion, in one embodiment.

One example of a bicycle powered energy generator will now be described in detail. FIG. 9 depicts a bottom perspective view of a bicycle mounted magnetic power generator system 900, in one embodiment. FIG. 10 depicts a top front perspective view of the bicycle mounted magnetic power generator system 900, of FIG. 9. FIG. 11 depicts a front view of the base ring 916 having magnets 918 used in the bicycle mounted magnetic power generator system 900, of FIG. 9, in one embodiment. FIG. 12A depicts an exploded view of the bicycle mounted magnetic power generator system 900, of FIG. 9. FIG. 12B depicts the strain gauges 804, electronics 914, and coil 912 when mounted on the bicycle mounted magnetic power generator system 900, without the base portion 1202, in one embodiment. FIGS. 9-12B are best viewed in light of the following discussion.

Bicycle mounted magnetic power generator system 900 includes an electronics module 902 mounted to an inner surface of bicycle crank 904 coupled to a bicycle frame 906 on bottom bracket 908. Crank 904 is operated via force exerted on a pedal (not shown) attached to crank 904 at pedal attachment point 910. Electronics module 902 may include any feature of electronics module 800 discussed above, and be used to operate any one of strain gauge configurations discussed above with respect to FIGS. 2-7.

Generator system 900 is shown as a magneto system for generating power. Electronics module 902 includes at least one coil 912 coupled with a power storage element, such as a battery. Coil 912 is coupled with electronics 914 for controlling power generation by coil 912. Coil 912 is mounted on crank 904 such that it is adjacent to a base ring 916 including a plurality of stationary magnets 918(1), 918(2), . . . 918(N). Base ring 918 may be coupled such that is stationary as the crank 904 rotates about bottom bracket 908. For example, base ring 918 may be mounted directly to frame 906, or to an intermediary part around bottom bracket 908 such that it does not rotate or otherwise move. As coil 912 is rotated due to pedaling by the rider, a voltage is generated at the leads of the coil 912 based upon magnetic fields produced by magnets 918.

As shown in FIG. 11, base ring 916 is mounted to frame 906 and includes a plurality of magnets 918(1)-918(N). Although shown with 22 magnets 918, it should be appreciated that there may be more or fewer magnets without departing from the scope hereof. Magnets 918 are shown having alternating north (N) and south (S) polarities. Therefore, as coils 912 pass by magnets 918, the coils generate alternating pulses of voltage depending on the polarity of the magnet 918. Electronics module 912 then rectify and filter this single to generate a smooth DC signal for storage in a power storage module (such as a rechargeable battery in power supply 824 of FIG. 8). The power supply then is capable of operating one or more electronic devices (such as controller 810 operating wireless interface 814 and strain gauges 804 having any of the configurations discussed above with regards to FIGS. 2-7). In alternate embodiments, magnets 918 all have the same polarity (e.g. N or S polarity).

Magnets 918 may further include various elements for focusing the magnetic field produced thereby to increase the power generated through coils 912. For example, the magnets 918 could include ferrous cups that focus the magnetic field at the coil 912. Additionally, magnets 918 may be formed from various materials to increase the magnetic field produced thereby. Magnets 918 may be formed of various rare earth metals, or alternatively may be electromagnets. Furthermore, the magnets 918 may be prism or cone shaped to focus their magnetic field at coil(s) 912.

Electronics 914 may further include algorithms for determining various aspects of the rider's performance. Where magnets 918 are regularly spaced around ring 916, the periodic nature of the output signal produced by coil 912 may be utilized by electronics to determine acceleration, rotation/minute, etc. In other words, coil 912 may be used as a rotary encoder based on the spacing between magnets 918.

As shown in FIG. 12A, housing may include a base portion 1202 including coil mounting location 1204. Base portion 1202 may couple with electronics 914 and be mounted adjacent strain gauge 804 which is attached to crank 904. In certain embodiments, base portion 1202 may further include a shield (not shown) for providing a magnetic field shield such that magnetic field generated by magnets 918 and coil 912 do not interfere with operation of strain gauges 804. As shown in FIG. 12B, when mounted onto crank 904, the coils 912 are adjacent strain gauges 804 and only take up minimal physical area on the inner surface of crank 904. As such, system 900 is easily installed on any crank 904. Therefore, any crank may be modified to include power generation system 900, and electronics module 800.

It should be appreciated that in another embodiment, a magnet could be placed on the crank 904, and one or more coils could be placed in ring 916 and connected to a power supply located on the frame. This power supply could be utilized to power or recharge a power supply located on the bicycle (such as on or in the frame 906).

Coils 912 are located adjacent to magnets 918 and spaced apart from magnets 918 a given distance. As such, crank 904 may include a spacing element (not shown) to set the distance that coils 912 are located from magnets 918. It should be appreciated that the closer the coil(s) 912 are located to magnets 918, the more power that is output at the leads of the coils.

Although not shown, electronics 902 may further include an outer housing that may or may not cover coil 912.

Figure 13:
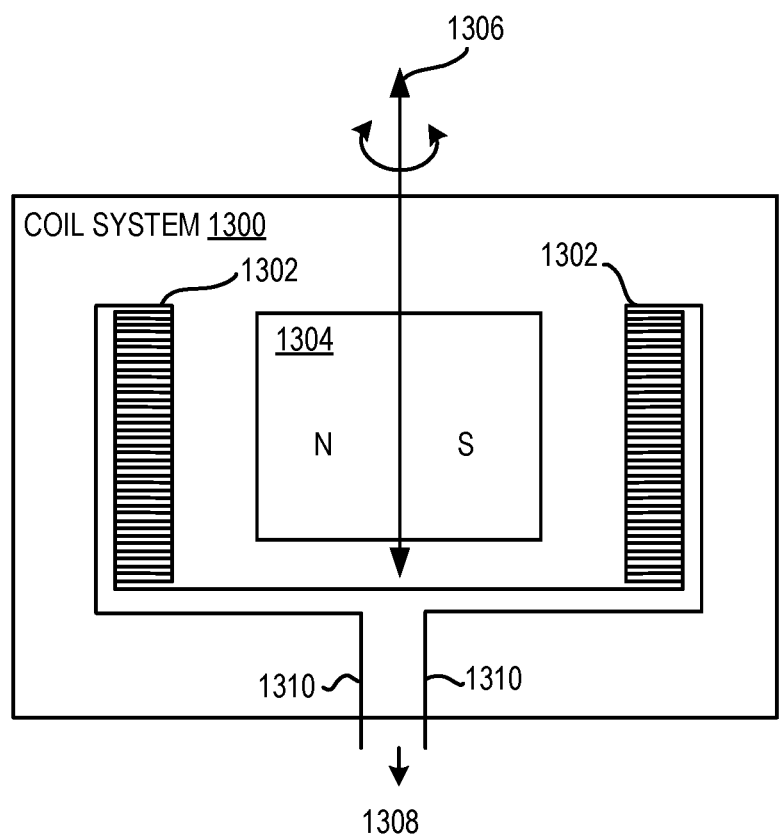
FIG. 13 depicts a coil system for use in the bicycle mounted power generator of FIGS. 9-12, in one embodiment.

FIG. 13 depicts a coil system 1300 for use in the bicycle mounted power generator 900, of FIGS. 9-12, in one embodiment. Coil system 1300 is an example of coil 912 and includes, stationary coil(s) 1302 surrounding an internal magnet 1304 that is rotatably mounted on axis 1306. Magnetic fields from magnets 918 within ring 916 (as discussed above) cause magnet 1304 within coil system 1300 to rotate about axis 1306. This rotation induces current in coils 1302 to produce an output 1308 at coil leads 1310. In operation, the magnetic field produced by magnets 918 located in base ring 916 is strong enough to rotate magnet 1304 about axis 1306, but not strong enough to negatively affect the output 1308 at coil leads 1310. In alternate embodiments, a magnetic shield may be placed between coils 1302 and base ring 916 such that the magnetic field produced by magnets 918 only affect magnet 1304 and do not induce electricity in coils 1302.

Combination of Features

Features described above as well as those claimed below may be combined in various ways without departing from the scope hereof. The following examples illustrate possible, non-limiting combinations the present invention has been described above, it should be clear that many changes and modifications may be made to the process and product without departing from the spirit and scope of this invention:

(A) A crank power measurement system measures one or more of force, torque, power, and velocity of the crank. The system includes a crank, two or more strain gauges located on a surface of the crank, and electronics for receiving strain data from the two or more strain gauges and determining at least one or more of bend-strain, shear-strain, and axial strain.

(B) In the system denoted as (A), the two or more strain gauges including a first and second bend-sensing strain gauges located away from opposing sides of the neutral axis.

(C) In either of the systems denoted as (A) and (B), the two or more strain gauges further including a third and fourth bend-sensing strain gauges.

(D) In the system denoted as (C), the third bend-sensing strain gauge being located between the neutral axis and the first bend-sensing strain gauge, the fourth bend-sensing strain gauge being located between the second bend-sensing strain gauge and the neutral axis.

(E) In the system denoted as (C), the third bend-sensing strain gauge being located adjacent and at substantially the same distance away from the neutral axis as the first bend-sensing strain gauge, the fourth bend-sensing strain gauge being located adjacent and at substantially the same distance away from the neutral axis as the second bend-sensing strain gauge.

(F) In any of the systems denoted as (A) through (E), the two or more strain gauges further including a first and second shear-sensing strain gauges.

(G) In any of the systems denoted as (A) through (F), the first shear-sensing strain gauge being symmetrically opposed to the second shear-sensing strain gauge.

(H) In any of the systems denoted as (A) through (G), the two or more strain gauges further including first and second axial-sensing strain gauges located on the neutral axis.

(I) In any of the systems denoted as (A) through (H), the first axial-sensing strain gauge being rotated 90 degrees from the second axial-sensing strain gauge.

(J) In any of the systems denoted as (A) through (I), the two or more strain gauges further including first, second, third, and fourth axial-sensing strain gauges.

(K) In any of the systems denoted as (J), two of the axial-sensing strain gauges being horizontally oriented along the crank, and two of the axial-sensing strain gauges being vertically oriented on the crank.

(L) In any of the systems denoted as (J) and (K), the first and second axial-sensing strain gauges being offset from the other strain gauges and towards a bottom bracket of the crank, and the third and fourth axial-sensing strain gauges being offset from the other strain gauges away from a bottom bracket of the crank.

(M) In any of the systems denoted as (A) through (L), the two or more strain gauges further including first, second, third, and fourth shear-sensing strain gauges.

(N) In any of the systems denoted as (A) through (M), the two or more strain gauges including a primary set of strain gauges, and a secondary set of strain gauges.

(O) In any of the systems denoted as (N), data acquired by the secondary set of strain gauges being utilized by the electronics to augment the accuracy of data acquired by the primary set of strain gauges.

(P) In either of the systems denoted as (N) and (O), the primary set of strain gauges being bend-sensing strain gauges.

(Q) In any of the systems denoted as (N) through (P), the secondary set of strain gauges being axial-sensing strain gauges.

(R) In any of the systems denoted as (N) through (P), the secondary set of strain gauges being shear-sensing strain gauges.

(S) A bicycle crank mounted power generator for generating power when the bicycle is being ridden by a user. The bicycle crank mounted power generator includes a base ring fixedly attached to a frame of the bicycle, the base ring circling a bottom bracket attached to a crank, a plurality of magnets coupled with the base ring, a coil system attached to the crank located adjacent to the plurality of magnets such that when the crank rotates about the bottom bracket, the coil generates an output at leads of the coil, and electronics configured to manipulate the output to at least one of power an electronic device or store the output in a power supply.

(T) In the bicycle crank mounted power generator denoted above as (S), the plurality of magnets having alternating magnets of opposing polarities.

(U) In either of the bicycle crank mounted power generators denoted as (S) and (T), the electronic device being any of the crank power measurement systems denoted as (A) through (R).

(V) In any of the bicycle crank mounted power generators denoted as (S) through (U), the power supply being a rechargeable battery supplying power to any of the crank power measurement systems denoted as (A) through (R).

(W) In any of the bicycle crank mounted power generators denoted as (S) through (U), the power supply being a super capacitor supplying power to any of the crank power measurement systems denoted as (A) through (R).

(X) In any of the bicycle crank mounted power generators denoted as (S) through (W), the magnets being electromagnets.

(Y) In any of the bicycle crank mounted power generators denoted as (S) through (W), the coil system including an internal magnet that rotates about an axis and surrounding coils, wherein a magnetic field produced by the plurality of magnets causes the internal magnet to rotate about the axis thereby producing electricity at output leads of the coils.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A crank measurement system, comprising:
   a crank;
   first, second, third, and fourth bend-sensing strain gauges located on one surface of the crank and oriented parallel to a neutral axis of the crank to sense bend strain induced in the crank, the first and third bend-sensing strain gauges being located above the neutral axis, the second and fourth bend-sensing strain gauges being located below the neutral axis;

first and second shear-sensing strain gauges located on the one surface of the crank and oriented to sense shear strain induced in the crank, the first shear-sensing strain gauge being located above the neutral axis, the second shear-sensing strain gauge being located below the neutral axis and oriented to mirror the first shear-sensing strain gauge about the neutral axis; and an electronics module configured to receive strain data from the first, second, third, and fourth bend-sensing strain gauges, and the first and second shear-sensing strain gauges, and determine from the strain data one or more of force, torque, and power applied to the crank.

2. The crank measurement system of claim 1, wherein:
the third bend-sensing strain gauge is located between the neutral axis and the first bend-sensing strain gauge; and
the fourth bend-sensing strain gauge is located between the neutral axis and the second bend-sensing strain gauge.

3. The crank measurement system of claim 1, further comprising third and fourth shear-sensing strain gauges located on the one surface of the crank and oriented to sense shear strain induced in the crank, the third shear-sensing strain gauge being located above the neutral axis, the fourth shear-sensing strain gauge being located below the neutral axis and oriented to mirror the third shear-sensing strain gauge about the neutral axis.

4. The crank measurement system of claim 3, further comprising:
a first axial-sensing strain gauge located on the one surface of the crank along the neutral axis, and oriented perpendicular to the neutral axis;
a second axial-sensing strain gauge located on the one surface of the crank above the neutral axis, and oriented 90 degrees relative to the first axial-sensing strain gauge;
a third axial-sensing strain gauge located on the one surface of the crank along the neutral axis, and oriented 180 degrees relative to the first axial-sensing strain gauge; and
a fourth axial-sensing strain gauge located on the one surface of the crank below the neutral axis, and oriented 270 degrees relative to the first axial-sensing strain gauge.

5. The crank measurement system of claim 1, further comprising first and second axial-sensing strain gauges located on the one surface of the crank, the first axial-sensing strain gauge being located above the neutral axis and oriented parallel to the neutral axis, the second axial-sensing strain gauge being located below the neutral axis and oriented perpendicular to the neutral axis.

6. The crank measurement system of claim 5, further comprising third and fourth axial-sensing strain gauges located on the one surface of the crank, the third axial-sensing strain gauge being oriented parallel to the neutral axis, the fourth axial-sensing strain gauge being oriented perpendicular to the neutral axis.

7. The crank measurement system of claim 5, wherein:
each of the first axial-sensing strain gauge and the first shear-sensing strain gauge is located between the neutral axis and the first and third bend-sensing strain gauges; and
each of the second axial-sensing strain gauge and the second shear-sensing strain gauge is located between the neutral axis and the second and fourth bend-sensing strain gauges.

8. The crank measurement system of claim 1,
further comprising an inertial sensor located on the crank;
wherein the electronics module is further configured to:
receive inertial-sensor data from the inertial sensor,
determine, from the inertial-sensor data, a rotation speed of the crank, and
determine, from the rotation speed and the strain data, the power applied to the crank.

9. The crank measurement system of claim 1, the electronics module being further configured to:
determine, from the strain data, a rotation speed of the crank, and
determine, from the rotation speed and the strain data, the power applied to the crank.

10. The crank measurement system of claim 1, the electronics module including a wireless interface to wirelessly communicate at least one of the force, torque, and power to one or more of a smart phone, bike computer, and computer.

* * * * *